United States Patent [19]
von der Heide et al.

[11] 4,153,554
[45] May 8, 1979

[54] APPARATUS FOR USE IN ARTIFICIAL KIDNEY SYSTEM

[75] Inventors: Jack von der Heide, Arlington; Robert J. Edelman; Murray R. McLeod, both of Dallas, all of Tex.

[73] Assignee: American Micro-Bionics Corp., Garland, Tex.

[21] Appl. No.: 770,789

[22] Filed: Feb. 22, 1977

[51] Int. Cl.² .................. B01D 13/00; B01D 31/00
[52] U.S. Cl. ................ 210/96 M; 210/135; 210/137; 210/197; 210/321 B
[58] Field of Search ............. 210/321 B, 85, 321 HT, 210/87, 90, 96 M, 195 R, 194, 197, 22, 137, 135

[56] References Cited

U.S. PATENT DOCUMENTS

| | | | |
|---|---|---|---|
| 3,238,021 | 3/1966 | Webber et al. | 23/259.1 |
| 3,441,136 | 4/1969 | Serfass et al. | 210/321 B |
| 3,506,126 | 4/1970 | Serfass et al. | 210/96 |
| 3,508,656 | 4/1970 | Serfass et al. | 210/321 B |
| 3,515,275 | 6/1970 | Bowman | 210/22 |
| 3,518,982 | 7/1970 | Timmins et al. | 210/321 B |
| 3,527,700 | 9/1970 | Goldhaber | 210/22 |
| 3,650,404 | 3/1972 | Versaci | 210/321 B |
| 3,754,649 | 8/1973 | Palubniak et al. | 210/103 |
| 3,795,318 | 3/1974 | Crane et al. | 210/321 B |
| 3,832,067 | 8/1974 | Kopf et al. | 210/321 B |
| 3,878,095 | 4/1975 | Frasier et al. | 210/321 B |
| 3,900,396 | 8/1975 | Lamadrid | 210/94 |
| 3,920,556 | 11/1975 | Bowman | 210/321 B |
| 3,946,731 | 3/1976 | Lichtenstein | 210/87 |
| 4,026,800 | 5/1977 | Friedrich et al. | 210/321 B |

OTHER PUBLICATIONS

Travenol Laboratories Hemoglobin Detector, Travenol Laboratories Inc., Morton Grove, Ill., 60059, 4/3/67.
"A New Compact Automatic Home Hemodialysis System", J. R. De Palma, E. A. Decker, A. Gordon, M. H. Maxwell, Trans. Amer. Soc. Artif. Int. Organs, 1968.
Travenol Laboratories, "RSP" Recirculating Single Pass Hemodialyzer Travenol Laboratories Inc., Morton Grove, Ill. 60059, 9/30/67.

*Primary Examiner*—Charles N. Hart
*Assistant Examiner*—David R. Sadowski
*Attorney, Agent, or Firm*—Hubbard, Thurman, Turner, Tucker & Glaser

[57] ABSTRACT

A machine is disclosed for use with an artificial kidney. The machine has three separately controllable pumps enabling delivery and return of a dialysate solution to an artificial kidney with precise control of various dialysate parameters such as temperature, pressure, conductivity, and flow rate.

The machine has redundant control and monitor circuits to assure safe operation. The monitor circuit is capable of causing the machine to stop dialysis if any one of various monitored parameters goes out of limits.

14 Claims, 14 Drawing Figures

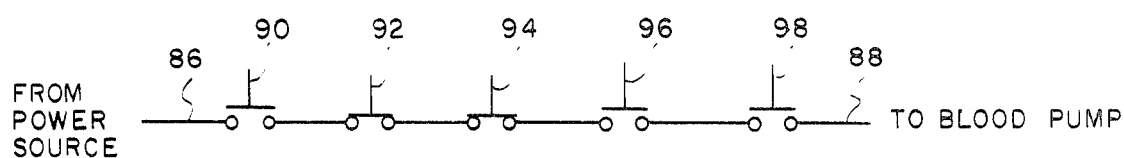
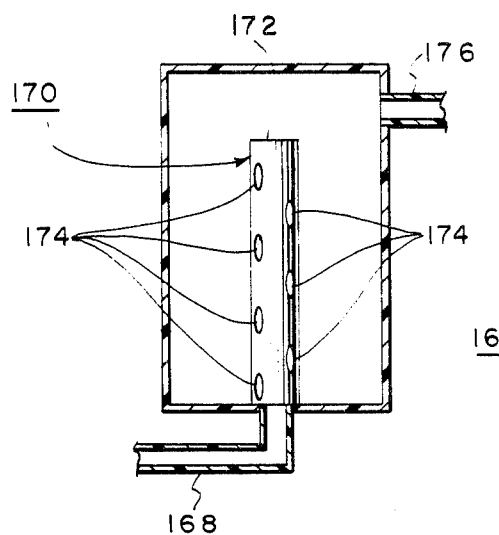
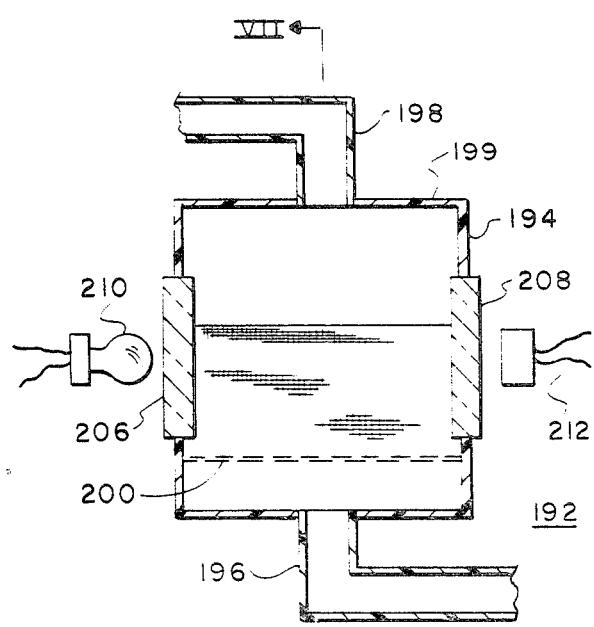
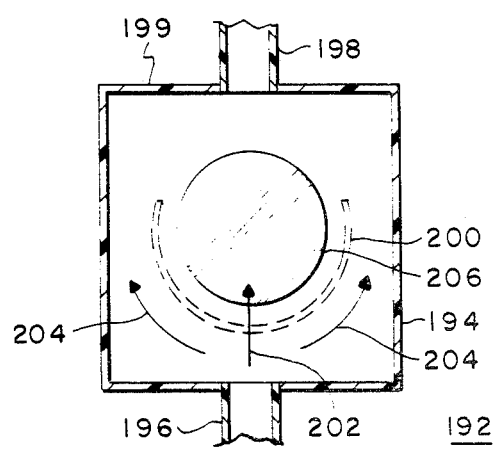

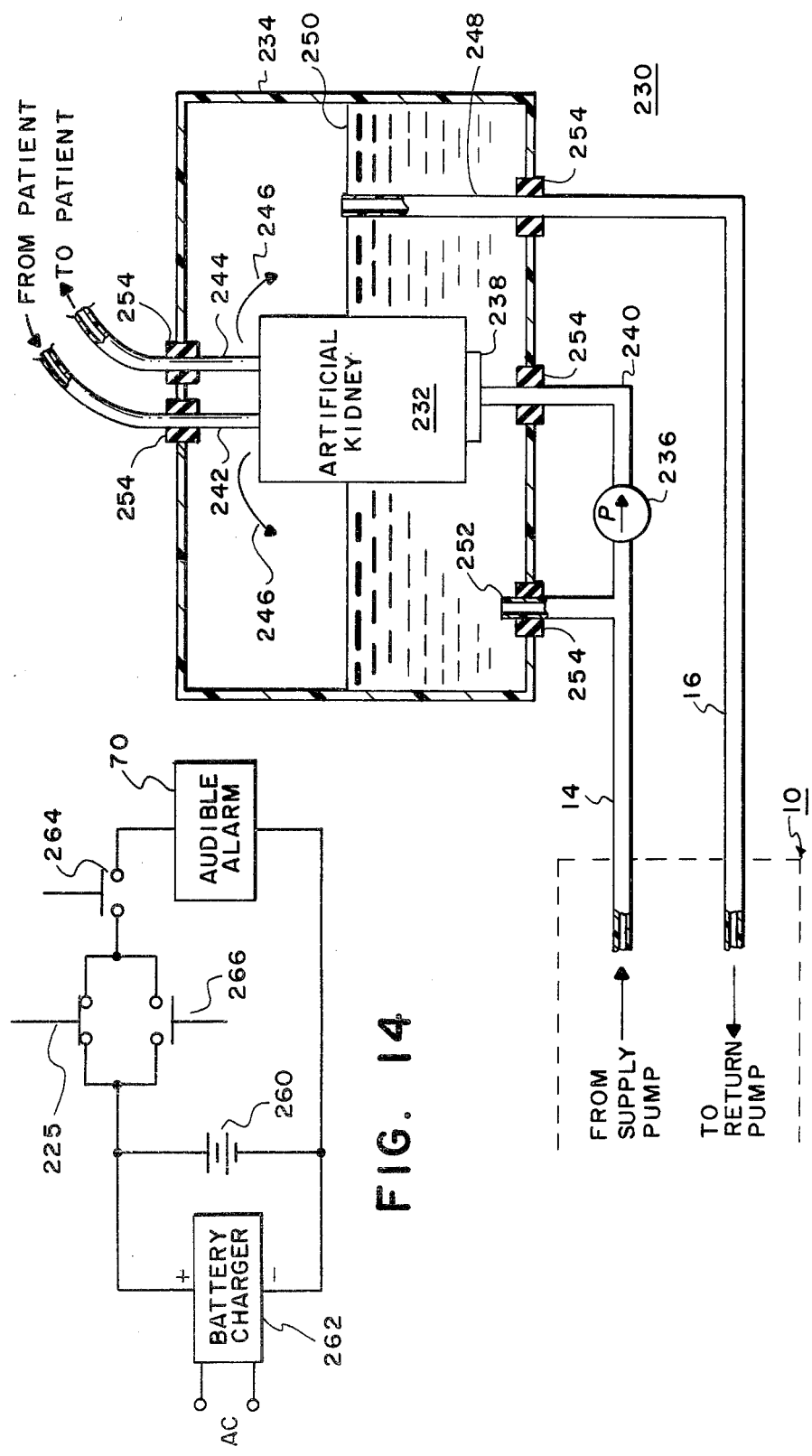

4,153,554

APPARATUS FOR USE IN ARTIFICIAL KIDNEY SYSTEM

BACKGROUND OF THE INVENTION

The present invention pertains to systems for preparing and delivering fluids to an artificial kidney in a controlled manner.

All artificial kidney systems have a common objective of removing toxins and excess body fluids from the bloodstream of a kidney-failure patient. Toxins are removed by dialysis, which is a chemical diffusion process using a semipermeable membrane which selectively permits the toxins to pass from the blood into a chemical solution referred to in the art as "dialysate". Excess body fluids are removed by developing a pressure differential across the semipermeable membrane (referred to as the "transmembrane pressure" or "TMP") which forces water molecules to pass from the blood into the dialysate.

Such basic functions occur in the artificial kidney or "dialyzer" portion of the system, the principal elements of which are the semipermeable membrane, input and output ports for the patient's blood, and input and output ports for the dialysate solution. The artificial kidney is an electrically passive component of the system, which works in response to the pressure of the fluids passing through its ports coupled with osmatic action in a manner known in the art.

The machine which delivers the dialysate solution to the artificial kidney is a complex electro-mechanical apparatus which functions within tightly controlled limits and which monitors various safety parameters. The present invention is directed to such a machine and to dialysate delivery systems in general.

SUMMARY OF THE INVENTION

In accordance with the present invention, an apparatus for delivering a dialysate solution to an artificial kidney comprises:

a system for controllably heating and proportioning a dialysate solution, monitoring various parameters, and automatically controlling dialysis in an artificial kidney external to the apparatus in accordance with certain safety criteria.

The novel features believed characteristics of the invention are set forth in the appended claims. The nature of the invention, however, as well as its essential features and advantages may be understood more fully upon consideration of an illustrative embodiment, when read in conjunction with the accompanying drawings, wherein:

BRIEF DESCRIPTION OF THE DRAWINGS

FIG. 3 is a schematic diagram of a blood pump control circuit;

FIG. 5 is a partially sectional elevation view of a mixing chamber;

FIGS. 6 and 7 are sectional views of a blood leak detector;

FIG. 13 is a partially sectioned elevation view schematically illustrating a canistor optionally used in a system of the present invention; and FIG. 14 is a schematic diagram of a lost voltage control circuit of a machine of the present invention.

DESCRIPTION OF THE PREFERRED EMBODIMENTS

The presently preferred embodiments of the invention will now be described with reference to the drawings, wherein like numerals refer to like parts in all figures.

Figure 1:
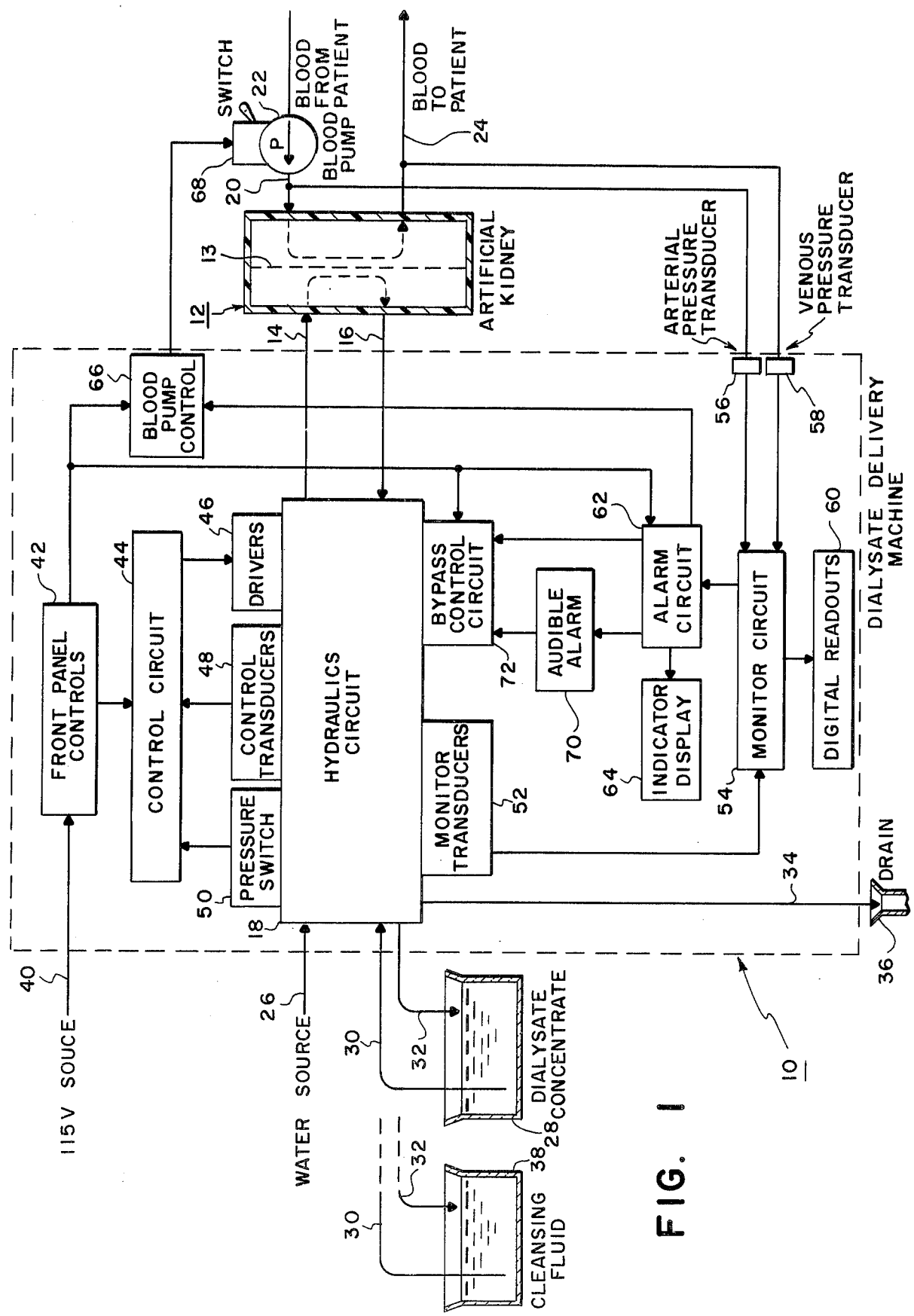
FIG. 1 is a schematic system diagram of the present invention.

FIG. 1 illustrates a system diagram of the present invention, the principal components of which are a dialysate delivery machine, contained within the dashed outline and indicated generally by reference numeral 10, and an artificial kidney, indicated generally by reference numeral 12.

The artificial kidney 12 is preferably a single pass type known in the art, which is a self-contained closed system permitting the development of a pressure differential across a semipermeable membrane 13. The machine 10 is linked to the artificial kidney 12 by a dialysate supply line 14 and a dialysate return line 16. A solution of dialysate of known constituents is pumped through the supply line 14 into the kidney 12 by a hydraulics circuit 18 of the machine 10.

Blood from a kidney-failure patient enters the artificial kidney 12 through an arterial supply line 20, after passing through a blood pump 22. A venous return line 24 carries processed block back to the patient.

During dialysis, a fresh supply of dialysate solution is constantly supplied to the kidney 12 by the machine 10, which prepares the solution by mixing water with a concentrated solution of dialysate in a predetermined ratio. Ordinary tap water may serve as a water source, which enters the hydraulics circuit 18 through water inlet line 26. A suitable container 28 serves to supply dialysate concentrate to the hydraulics circuit 18 through concentrate inlet line 30. Unused concentrate is returned to the container 28 through outlet line 32. Used dialysate solution is passed through a drain line 34 to a drain 36 of suitable capacity. In order to clean the hydraulics circuit 18, the inlet and outlet lines 30 and 32 are inserted in a container 38 of a suitable cleansing fluid known in the art, and the machine 10 is switched into a sterilize mode to be described below.

Electrical power is supplied to the machine 10 by line 40 from a single phase, 60 Hz source of 115 volts with a 20 ampere rating. Front panel controls 42 are provided for receiving system commands and parameter control settings from a human operator. Information from the conrols 42 is communicated to a control circuit 44. The control circuit 44 in turn communicates with drives 46 which power the hydraulics circuit 18. A set of control transducers 48 feeds back information to the control circuit 44 enabling accurate operation of the hydraulics circuit 18. A pressure switch 50 communicates with the hydraulics circuit 18 to determine if there is sufficient pressure in the water inlet line 26 to operate the machine 10. A set of monitor transducers 52 provides system redundancy by checking a number of monitored parameters. A monitor circuit 54, which includes means on the panel for setting parameter limits, collects electronic data from the monitor transducers 52 and performs certain computations.

In addition to monitoring various parameters within the machine 10, circuit 54 also monitors data from the blood lines 20 and 24. Transducers 56 and 58 communicate with blood lines 20 and 24 respectively, and send electronic arterial and venous pressure data to the monitor circuit 54. The arterial and venous pressures are defined to be the pressures of the blood entering and leaving the artificial kidney 12. The monitor circuit 54 is provided with means for displaying both limit settings and data from the transducers 52, 56 and 58 on digital readouts 60.

Additionally, the limit settings and all monitored data are sent to an alarm circuit 62, which detects any out-of-limits condition and indicates which parameters are out of limits by means of a display 64. The alarm circuit 62 sends an enabling signal to a blood pump control circuit 66 only when all monitored parameters come within limits. When an enabling signal is sent from the alarm circuit 62 coincidentally with RUN and DIALYZE commands from the panel controls 42, the control circuit 66 provides power to the blood pump 22 through a manual switch 68 disposed thereon. A DIALYZE command also activates an audible alarm 70 coincident with the alarm circuit 62 detecting any out-of-limits condition. Finally, the alarm circuit 62 communicates with a bypass control circuit 72, which causes the hydraulics circuit 18 to divert the supply of dialysate from the artificial kidney 12 whenever the audible alarm 70 sounds or whenever a RUN command is generated coincident with any of several selected parameters being out of limits as will be described in more detail below.

In some systems certain additional accessories are used in conjunction with the blood pump 22. For example, a heparin infusion device (not shown) may be connected to blood line 20 to inhibit clotting in a known manner. Such accessories may be controlled in like manner to the control of the blood pump 22 by means of power receptacles located on the back panel (not shown) of the machine 10. Power is supplied to such accessory receptacles as well as a blood pump receptacle through the blood pump control circuit 66.

Figure 2:
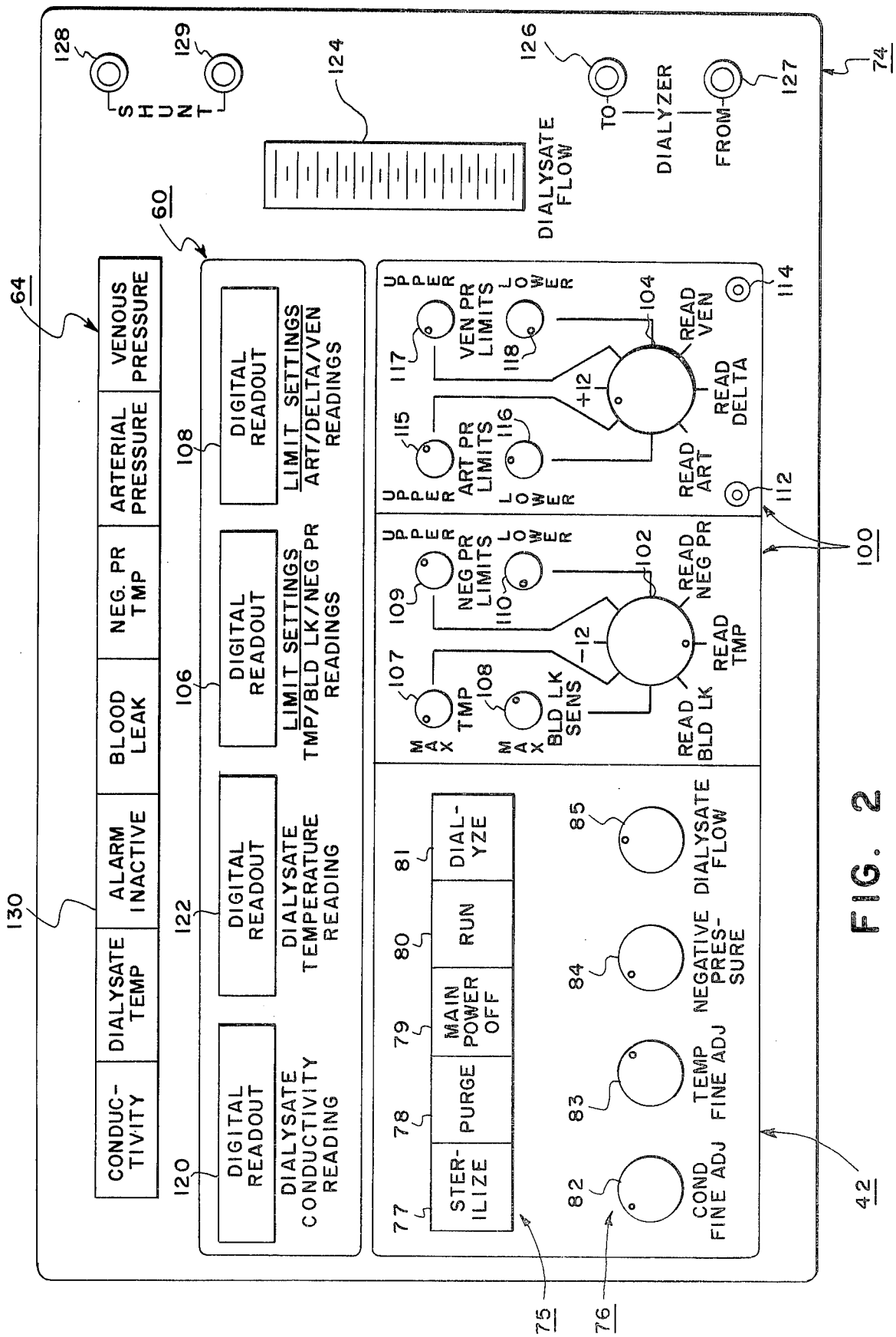
FIG. 2 is a schematic representation of a front control panel of a machine of the present invention.

FIG. 2 illustrates a front control panel 74 of the machine 10 of FIG. 1. The controls 42 consists of a gang 75 of system command switches and a group 76 of control knobs. Four of the command switches are mechanically interlocked to be mutually exclusive, so that no two of the four may be engaged at the same time. The four mechanically interlocked switches are STERILIZE 77, PURGE 78, MAIN POWER 79, and RUN 80. A DIALYZE switch 81, which is mechanically independent of the other switches in the gang 75, controls both the blood pump 22 and the audio alarm 70 described above.

The group of control knobs 76 consists of a conductivity fine-adjust knob 82, a temperature fine-adjust knob 83, a negative-pressure control knob 84, and a dialysate-flow control knob 85. Knobs 82 and 83 permit adjustment of the desired conductivity and temperature within internally fixed limits. Knobs 84 and 85 are calibrated to permit a range of negative pressure and flow settings, the effects of which will be discussed below.

Referring briefly to FIG. 3, the interaction of the command switches 75 with the control of the blood pump power will be described. FIG. 3 illustrates a blood pump control circuit 66 comprising a series arrangement of contacts disposed between an incoming power line 86 and a power line 88 for supplying the blood pump.

A power-on switch 90 is closed whenever either the STERILIZE 77, PURGE 78 or RUN 80 switches (see FIG. 2) are engaged. Pushing the MAIN POWER switch 79 opens the switch 90. A normally closed switch contact 92 is opened whenever the STERILIZE switch 77 is engaged. Similarly, a second normally closed switch contact 94 is opened whenever the PURGE switch 78 is engaged. Therefore, it will be apparent that having all three switches 90, 92 and 94 closed simultaneously is only possible by engaging the RUN switch 80.

Disposed in series with the contacts of switches 90, 92 and 94 are two normally open switch contacts 96 and 98. Engaging the DIALYZE switch 81 closes switch 96. The contacts of switch 98 are closed by an enabling signal from the alarm circuit 62 (see FIG. 1) generated only when no parameters are out of limits. Thus, power is supplied to the blood pump power line 88 only when RUN 80 and DIALYZE 81 are engaged and no parameters are out of limits.

Referring again to FIG. 2, a monitor portion 100 of the panel 74 will now be described. Multi-function switches 102 and 104 permit selection of the parameter to be displayed by digital readouts 105 and 106 respectively. The digital readouts 105 and 106 display both monitor limit settings and monitor readings. In particular, the monitor readings of TMP (transmembrane pressure), blood leak, and negative pressure may be displayed on readout 105 by selectively positioning switch 102. (The significance of these parameters will be discussed below with reference to FIG. 4.) The monitor limit settings of TMP maximum limit, blood leak sensitivity maximum limit, and negative pressure upper and lower limits may be adjusted by calibrated control knobs 107, 108, 109 and 110 respectively, the settings of which may be displayed on readout 105 by selectively positioning switch 102. The monitor readings of arterial pressure, delta pressure (arterial less venous), and venous pressure may be displayed on readout 106 by selectively positioning switch 104. Arterial and venous pressure data from transducers 56 and 58 (see FIG. 1) are inputted by fittings 112 and 114 on the front panel 74. The monitor limit settings of arterial pressure upper and lower limits, and venous pressure upper and lower limits may be adjusted by calibrated control knobs 115, 116, 117 and 118 respectively, the settings of which may be displayed on readout 106 by selectively positioning switch 104.

Multi-function switches with eight positions are standard commercial items. Each switch 102 and 104 may conveniently have an additional position (shown in FIG. 2 as the vertical position) for displaying additional data on readouts 105 and 106 respectively. For example, it may be desirable in certain applications to include readings for dialysate pH and chloride ion concentration. In the presently preferred embodiment, however, the eighth position on each switch 102 and 104 is used to check the voltage output of two internal power supplies, which provide a negative 12 volts and a positive 12 volts to the machine's electronic circuitry.

Additional digital readouts 120 and 122 are provided for giving continuous readout of dialysate conductivity and temperature. A flow indicator 124 provides visual indication of the actual flow rate of dialysate being supplied to an artificial kidney. Ports 126 and 127 are provided for attaching dialysate supply and return lines to the machine 10 for connection with an artificial kidney. As a convenience for cleaning supply and return lines (see lines 14 and 16 in FIG. 1) during sterilizing and purging operations, the lines may be shunted by connection to shunt ports 128 and 129.

Should one of the monitored parameters be out of limits while operating with the DIALYZE switch 81 engaged, an audible alarm (70 in FIG. 1) is activated and the offending parameter is indicated by lighting one light in a display bank of alarm indicator lights 64. When the machine 10 is operating with the DIALYZE switch 81 disengaged, the audible alarm 70 is inactive, which is positively indicated by light 130 being lit.

Now referring to FIG. 4, the operation of the hydraulics circuit 18 will be described.

Cold tap water enters the hydraulics circuit 18 through inlet line 26 where the flow is controlled by an inlet valve 132 and a purge valve 134. The valves 132 and 134 are solenoid operated and are normally closed so that water cannot enter the hydraulics circuit 18 in the absence of electrical power. The inlet valve 132 is opened whenever the power is turned on by engaging either STERILIZE 77, PURGE 78, or RUN 80 on the panel 74 (see FIG. 2). The purge valve 134 is opened only by engaging the PURGE switch 78. When the purge valve 134 is opened, water is permitted to flow through a restriction 135 into concentrate inlet line 30. When power is on, water passes through the inlet valve 132 to a pressure regulator 136, which lowers the water pressure to 2 psig. If the water source has insufficient pressure (i.e., less than 2psig), a pressure switch 50 signals the control circuit 44, which automatically shuts down the hydraulic circuit 18 until sufficient water pressure returns.

Next, the water enters a heater 138, which raises the water temperature to a sufficient level so that dialysate supplied to an artificial kidney will be at about normal body temperature. The heater 138 is controlled by a first of two control thermistors 139, which is cooperatively disposed in proximity to the heater 138. Next, the water flows into a float tank 140, which comprises a float-controlled water-inlet valve (not shown) enabling the tank 140 to be filled with a controlled volume of water. Air bubbles are removed from the tank 140 by means of a diaphragm-type vacuum pump 142, which pulls a partial vacuum of about minus 10 psig on the float tank 140 and passes air out a vent 143. The water is then drawn from the float tank 140 by a supply pump 144, which is preferably a gear pump of a standard commercially available type, and boosted back to about +5 psig (which is maintained by regulator 182 described below). A deaerator 146 removes additional air from the water by passing the water over a vertical baffle (not shown) near an upper air space which is in communication with the top of the float tank 140 by means of line 148 having a restriction 150. Air bubbles in the water line do not endanger the patient; however, they render inoperative the artificial kidney's semipermeable membrane (see numeral 13 in FIG. 1). The restriction 150 preferably comprises a needle valve not shown adapted with the float tank 140 to maintain the 5 psig pressure in the deaerator 146 and thus in the water as it leaves the deaerator 146. At that point a second control thermistor 152 feeds back the water temperature to the heater 138 through the control circuit 44.

With the water at an appropriate temperature and pressure and essentially free of air bubbles, it is ready to be mixed with dialysate concentrate to provide dialysate solution for passage through an artificial kidney. Accordingly, dialysate concentrate is supplied through inlet line 30 where it is pumped through branches 154 and 156 by a self-priming concentrate pump 158. A restriction 160 is disposed between branch 156 and outlet line 32, thereby permitting the pump 158 to develop an appropriate pressure in branch 154 to force a portion of the concentrate into the heated water through an injection orifice 162, which preferably comprises a 21 gauge syringe needle (not shown) extending into the water line. A suitable restriction 160 is a tube having about a 1.5 millimeter inside diameter. The relative sizes of the openings in the restriction 160 and the injection orifice 162 are chosen to permit flexibility in the operational speed range of the concentrate pump 158.

The proportioned solution of water and dialysate concentrate, which is simply referred to as "dialysate", flows into a conductivity cell 164, which provides an electrical measurement of the proportion of concentrate to water. The conductivity fine adjust knob 82 on the front panel 74 provides a means for compensating for ions initially present in the water. The dialysate conductivity measured by the cell 164 is fed into the control circuit 44 for adjusting the speed of the concentrate pump 158 with respect to the supply pump 144. The speed of the concentrate pump 158 is servo-controlled in such manner only when the RUN switch 80 is engaged. The speed of pump 158 is adjusted until one part of concentrate is being injected for every 34 parts of water flowing past the orifice 162 in accordance with present dialysis techniques.

By positioning the control-conductivity cell 164 immediately downstream of the injection orifice 162, a minimum servo-loop lag time is achieved, which correspondingly minimizes the conductivity deviations from the reference level set by control knob 82 on the front panel 74.

From the conductivity cell 164, the dialysate then flows into a mixing chamber 166 for damping conductivity and temperature variations, the details of which are shown in FIG. 5. Dialysate flows through an inlet line 168 into a pipe 170 disposed within the chamber 166. The pipe 170 is closed at its end 172 remote from the inlet 168; however, a plurality of small orifices 174 are disposed along the length of the pipe 170 causing incoming dialysate to be distributed and mixed within the chamber 166. Finally the mixed dialysate flows through an outlet 176 under the driving pressure of the supply pump 144.

Referring again to FIG. 4, the temperature and conductivity of the dialysate emerging from the mixing chamber 166 are measured by transducers consisting of a monitor thermistor 178 and a monitor conductivity cell 180 which send corresponding electrical data to the monitor circuit 54. At this point in the dialysate solution supply branch it may be desirable to include electrodes (not shown) for measuring dialysate pH and chloride ion concentration, which may be displayed on readouts 105 and 106 described above.

A pressure regulator 182 maintains a pressure of about 5 psig back upstream to the supply pump 144. Accordingly it is possible to maintain a steady flow of dialysate out to an artificial kidney, since the supply pump 144 has a constant pressure of about 5 psig to work against.

Dialysate passes from the pressure regulator 182 into a so-called "3-way" valve 184, referred to as such since it has three paths of flow, consisting of one inlet path and two alternative outlet paths. Solenoid operated 3-way valves are standard commercially available items. In the energized state, the 3-way valve 184 is in what will be referred to in this specification as the "bypass" position, which diverts the flow of dialysate down a bypass line 186. If the 3-way valve 184 is not energized by the bypass control circuit 72, the valve 184 will be in the "open" position, which permits the dialysate to flow out through the flow indicator 124 to the output port 126 where it leaves the hydraulics circuit 18.

Dialysate returning from an artificial kidney reenters the hydraulics circuit 18 through the return port 127. Effluent dialysate reentering through the return port 127 as well as any bypassed dialysate from line 186 is pumped out drain line 34 by a return pump 188. As the dialysate flows toward the return pump 188, its pressure is monitored by transducer 190. During dialysis, a negative pressure (i.e., a partial vacuum) exists in the returning dialysate. The transducer 190 measures such negative pressure.

Referring briefly back to FIGS. 1 and 2, the pressures from the blood side of the semipermeable membrane 13 are returned through fittings 112 and 114 to transducers 56 and 58 in the machine 10, which send corresponding electrical pressure data to the monitor circuit 54. The pressure across the membrane 13 determines the fluid removal rate of the artificial kidney 12. This transmembrane pressure (TMP) is a function of the arterial and venous pressures and the negative pressure of the returning dialysate. Therefore, the negative pressure may be used to control the TMP, which in turn determines the rate of fluid removal from the patient's blood.

Referring again to FIG. 4, the transducer 190 sends negative pressure data to both the control circuit 44 and the monitor circuit 54. The negative pressure level may be varied by varying th speed of the return pump 188. After passing through the return pump 188, used dialysate passes through a blood leak detector 192, which checks the dialysate for the presence of blood before the dialysate is passed out the drain line 34 and sends a corresponding signal to the monitor circuit 54.

Now referring to FIGS. 6 and 7, the details of a preferred blood leak detector will be described. The blood leak detector 192 comprises a chamber 194 through which returning dialysate is caused to pass. The chamber has an inlet port 196 located at the bottom through which dialysate enters, and an outlet port 198 located at the top 199 through which dialysate exits. A screen 200, which is preferably trough shaped as viewed in FIG. 7, is disposed in the chamber 194 between the inlet port 196 and outlet port 198. The screen 200 permits liquid to pass through with little resistance as indicated by the arrow 202; however, due to the phenomenon of surface tension, air bubbles which could otherwise interfere with the operation of the detector 192 are caused to pass around the screen 200 as indicated by the arrows 204.

Light is directed along a path above the screen 200 transverse to the flow of dialysate. In a presently preferred embodiment, the light enters through a green window 206, and exits through a clear window 208. A light bulb 210 directs white light at the window 206, which passes green light through the flow of dialysate and out the other side of the chamber 192 through window 208. Exiting green light through window 208 impinges upon a photocell 212, which is highly sensitive to green light and relatively insensitive to light outside the green spectrum. Such a photocell is presently commercially available, a suitable example of which is type number CL705HL available from Clairex Inc.

Since red blood cells absorb all but red light, the presence of blood in the dialysate flowing through the detector 192 will absorb some of the green light, thereby reducing the intensity of light impinging on the photocell 212 in direct proportion to the amount of blood per unit volume of dialysate. Accordingly, the signal from the photocell 212 may be calibrated to give a quantitative reading of blood in the dialysate returning from the artificial kidney. It should be noted, however, that any narrow band of light outside of the red band may be used effectively in a blood leak detector of the type described, provided the photocell is selectively sensitive to the band of light being passed through the chamber. For example, the combination of a blue filter in place of the window 206 and a blue-light-sensitive photocell in place of the cell 212 will be effective to provide a high degree of sensitivity to red blood cells passing through the chamber 194.

The blood leak detector 192 is, of course, also responsive to any agent which interferes with the passage of light through the chamber 194. For example, film deposits may form on the windows 206 and 208 inside the chamber, thereby interfering with light passage through to the photocell 212. Such films, which are not uncommon, cause the photocell 212 to give a false reading of the presence of blood. Such films may be removed chemically from the windows 206 and 208 during sterilization of by physically opening the blood leak detector 192 by removing the top 199 which is held in place by screws (not illustrated), and cleaning the windows 206 and 208 through the open top of screen 200. Alternatively, dialysis may be performed if the windows 206 and 208 are not too dirty, while still maintaining accurate detection of a blood leak in a manner which will now be described.

The blood leak alarm limit may be adjusted by means of a knob 108 on the front panel 74 of FIG. 2. The range of sensitivity is from 0 to 700 parts per million of blood in the returning dialysate. Therefore, prior to starting dialysis it is possible to adjust for any false reading of the blood leak detector 192. The switch 102 may be turned to "bld. lk." to display the reading of the detector 192 on the digital readout 105. Since no blood flows into the artifical kidney unless the DIALYZE switch 81 is engaged, readout 105 gives a false reading of blood presumably due to a deposit on the windows 206 and 208 of the blood leak detector 192. Accordingly the blood lead sensitivity limit 108 may be adjusted to exceed the "false reading" by some amount not to exceed the maximum limit of 700 ppm. Should the "false reading" exceed 700 ppm, the blood leak detector 192 must be cleaned, since the machine 10 will not permit dialysis to take place, there being no provision for manually overriding the alarm circuit 62 or any of the monitoring transducers including the blood leak detector 192. Nevertheless, should the "false reading" be somewhat less than 700 ppm, the sensitivity control knob 108 provides a means for adjusting the initial reference level of blood leak used by the alarm circuit 62, thereby compensating for a slightly dirty blood leak detector 192.

Now the modes of operation of the system will be described with particular reference to the command switches 75 shown in FIG. 2 and the monitor and alarm functions of the machine described above in conjunction with FIG. 1. The power may be turned on only by engaging one of the three command switches consisting of STERILIZE 77, PURGE 78, or RUN 80. When power is on, the machine 10 may enter one of six modes of operation which by definition comprise: a sterilize mode, a purge mode, a set-up mode, a supply mode, a dialyze mode, and an alarm mode. The sterilize mode occurs when the STERILIZE switch 77 is engaged and the DIALYZE switch 81 is disengaged. The purge mode occurs when the PURGE switch 78 is engaged and the DIALYZE switch 81 is disengaged. The set-up mode occurs when the DIALYZE switch 81 is disengaged, the RUN switch 80 is engaged, and an out-of-limits condition is detected for either temperature, conductivity or blood leak. The supply mode occurs when the DIALYZE switch 81 is disengaged, the RUN switch 80 is engaged, and each of the parameters of temperature, conductivity and blood leak are within limits. The dialyze mode occurs when the DIALYZE switch 81 is engaged, the RUN switch 80 is engaged, and no monitored safety parameters are out of limits. The alarm mode occurs when the DIALYZE switch 81 is engaged and any parameter out-of-limits condition is detected.

Figure 8:
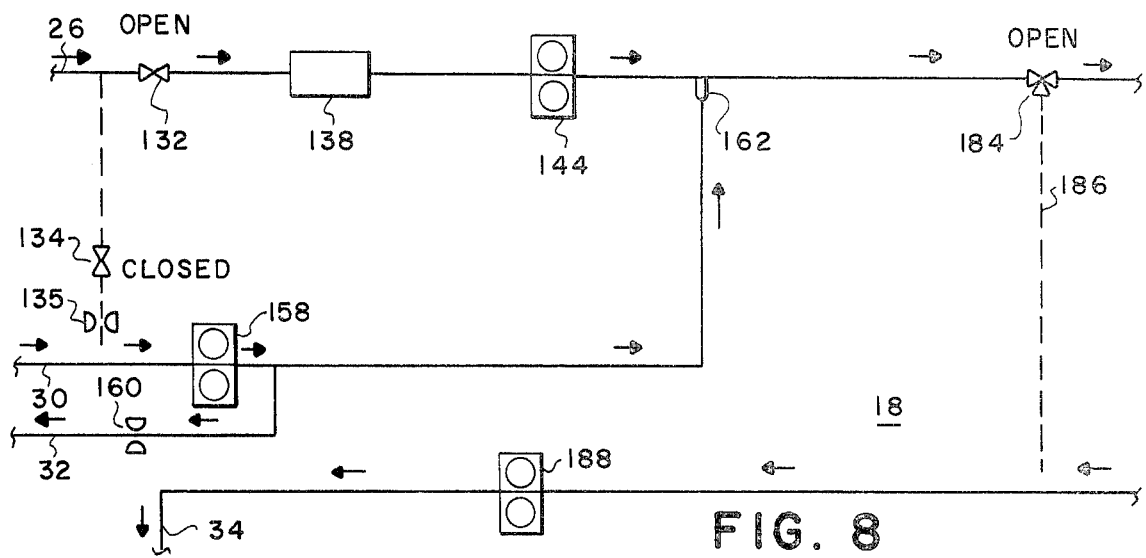
FIGS. 8, 9 and 10 schematically illustrate various operational flow paths of the hydraulics circuit of FIG. 4.

Now referring to FIGS. 8, 9 and 10, the various flow paths of the hydraulics circuit 18 will be described, wherein arrows indicate fluid flow directions and dashed lines indicate closed paths. In addition, many of the components of the hydraulics circuit 18 have been left out of FIGS. 8, 9, and 10 for ease of illustration.

The sterilize, supply and dialyze modes have the same flow path as will now be described with particular reference to FIG. 8. Engaging either the STERILIZE switch 77 or the RUN switch 80 turns on the power causing the inlet valve 132 to open. In either the sterilize, supply or dialyze modes, by definition the purge valve 134 is closed and the 3-way valve 184 is open, which produces the flow path indicated by the arrows. In the sterilize mode, the lines 30 and 32 are placed in a container of cleansing fluid; while in the supply and dialyze modes, the lines 30 and 32 are placed in a container of dialysate concentrate. In either case, fluid flows out of the circuit 18 through the 3-way valve 184. In addition, the supply and dialyze modes differ from the sterilize mode in that in the sterilize mode the power to the heater 138 is off and pumps 144, 158 and 188 all run at the same speed. During the supply and dialyze modes of operation, on the other hand, the RUN switch 80 is engaged, which causes power to be supplied to the heater 138 and activates servo-control of the heater 138 and pumps 144, 158 and 188 by means of feedback from the control transducers 48 (i.e., thermistors 139 and 152, conductivity cell 164, and negative pressure transducer 190). Additionally, by definition power is supplied to the blood pump 22 by means of circuit 66 when the machine 10 is operating in the dialyze mode (see FIGS. 1 and 3). When the switch 68 for manually controlling the blood pump 22 is turned on, the machine 10 takes over control of the blood pump 22.

Another unique feature of the sterilize mode is that the pressure switch 50 is electrically bypassed when the STERILIZE switch 77 is engaged, which permits sterilization of the water supply branch of the hydraulics circuit 18 as will now be described with reference to FIGS. 1 and 4. By placing the water inlet line 26 in the container of cleansing fluid 38 and engaging the STERILIZE switch 77, cleansing fluid may be drawn into the line 26 by the suction of the pumps 142 and 144. The operation of both pumps 142 and 144 together quickly pulls a partial vacuum in the float tank 140, which draws cleansing fluid into the line 26 and thereafter pumps the cleansing fluid down line. The cleansing fluid may go out to an artificial kidney or may conveniently be shunted by connecting lines 14 and 16 to the shunt ports 128 and 129. A closed sterilization loop may be formed by placing the concentrate lines 30 and 32 and the drain line 34 in the container 38 along with the water inlet line 26.

Figure 9:
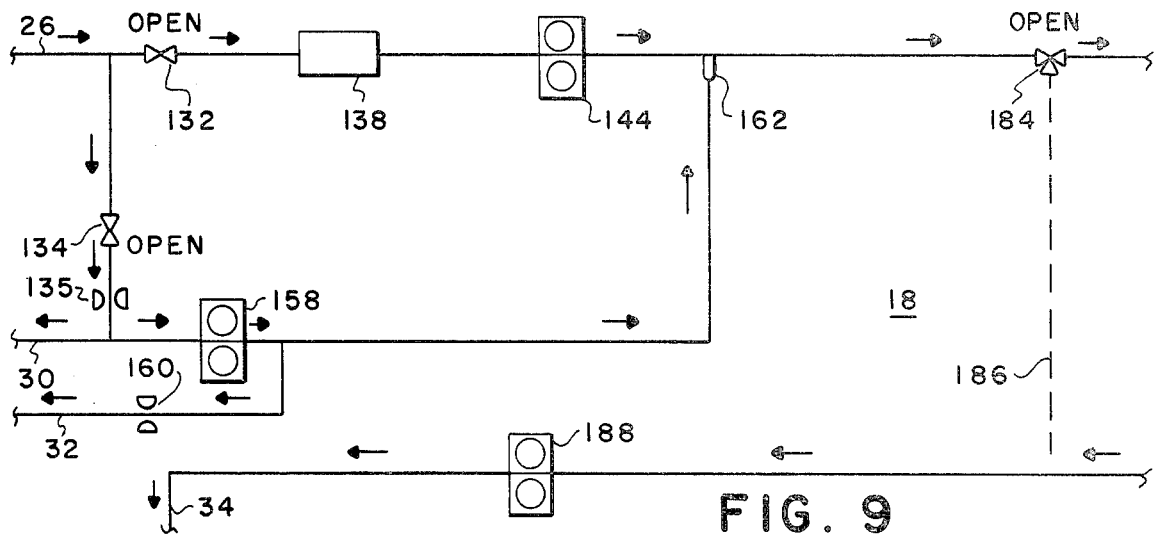

The purge mode is similar to the sterilize mode except that the purge valve 134 is opened, resulting in the flow path depicted in FIG. 9. The purge mode enables the operator to flush water from the inlet line 26 through the hydraulics circuit 18 (except for the bypass line 186) as well as through an artificial kidney. The water flows through purge valve 134 and through the restriction 135 at a rate faster than can be drawn through pump 158, such that some water washes out the inlet line 30. The restriction 135 is narrow enough, however, so that a substantial portion of the water flowing in through inlet 26 continues through valve 132, eventually passing out through the 3-way valve 184.

Figure 10:
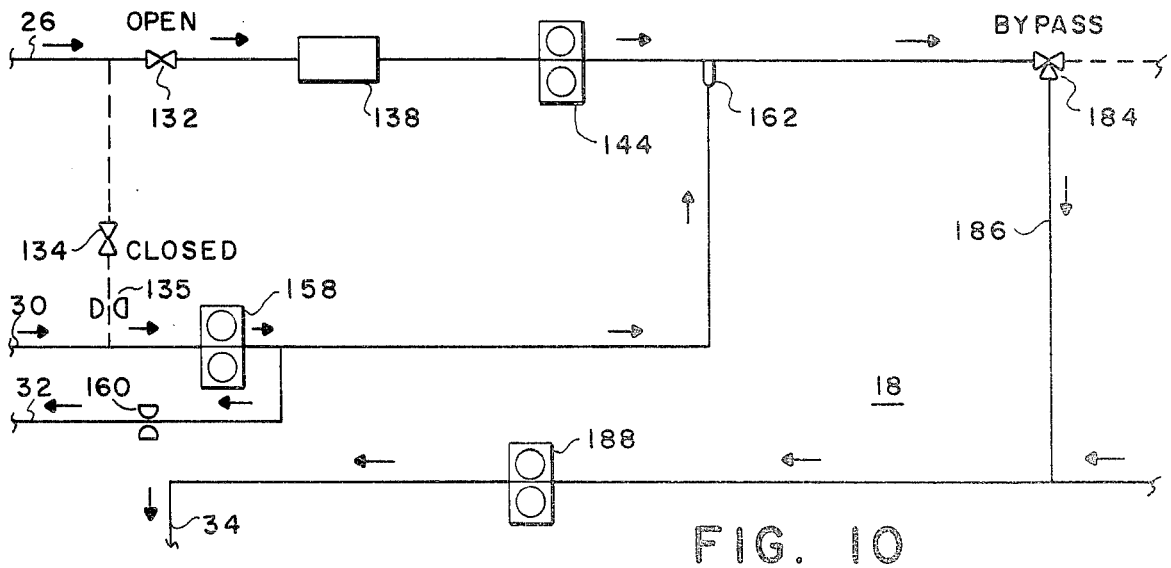

The set-up and alarm modes have the same flow path as depicted in FIG. 10. Valve 132 is open, valve 134 is closed, and valve 184 is in the bypass position, resulting in the flow path indicated by the arrows. The set-up and alarm modes protect the patient from improper dialysate reaching the artificial kidney. In addition, the set-up mode provides a means for sterilizing or flushing the bypass line 186, which may be achieved by pushing the RUN switch 80 after operating in the sterilize or purge modes.

The machine 10 is made ready for dialysis in the following manner. Briefly referring back to FIGS. 1 and 2, lines 14 and 16 are attached to the artificial kidney 12, lines 30 and 32 are placed in a container 38 of cleansing fluid and the STERILIZE switch 77 is engaged. After a sufficient elapsed time, the RUN switch 80 is engaged, which sterilizes the bypass line 186. The OFF switch 79 is then pushed, which shuts down the sytem, and the lines 30 and 32 are placed in the drain 36. The PURGE switch 78 is then engaged to restart the system causing water to flush out the cleansing fluid. The RUN switch 80 is then engaged to flush the bypass line 186, after which the OFF switch 79 is pushed and the lines 30 and 32 are placed in the container 28 of dialysate concentrate. The RUN switch 80 is then engaged and the machine 10 goes into the set-up mode discussed above in conjunction with FIG. 10. After a period of time, the machine 10 automatically switches into the supply mode (see FIG. 8) upon temperature and conductivity coming within limits. When all monitored parameters come within limits as indicated by all the lights in display 64 being out except the alarm inactive light 130, the DIALYZE switch 81 is engaged putting the machine 10 in the dialyze mode.

In the dialyze mode, all lights in display 64 are out including light 130, and the audible alarm 70 is armed and ready to sound if any monitored parameter goes out of limits. In addition, the blood pump 22 should be running, since it is being supplied power by the blood pump control circuit 66.

Should a monitored parameter go out-of-limits during the dialyze mode, the machine 10 automatically enters the alarm mode. In the alarm mode, the blood pump 22 is shut off, an audible alarm 70 sounds, and the 3-way valve 184 is switched into the bypass position.

It should be mentioned that in addition to the six operationally defined modes discussed above, there exists a command error condition which can occur if machine 10 is operating in the dialyze mode and someone inadvertently engages either the STERILIZE switch 77 or the PURGE switch 78. Such action disengages the RUN switch 80, activates the audible alarm 70, shuts off the blood pump 22, and by definition, terminates operation in the dialyze mode.

Figure 11:
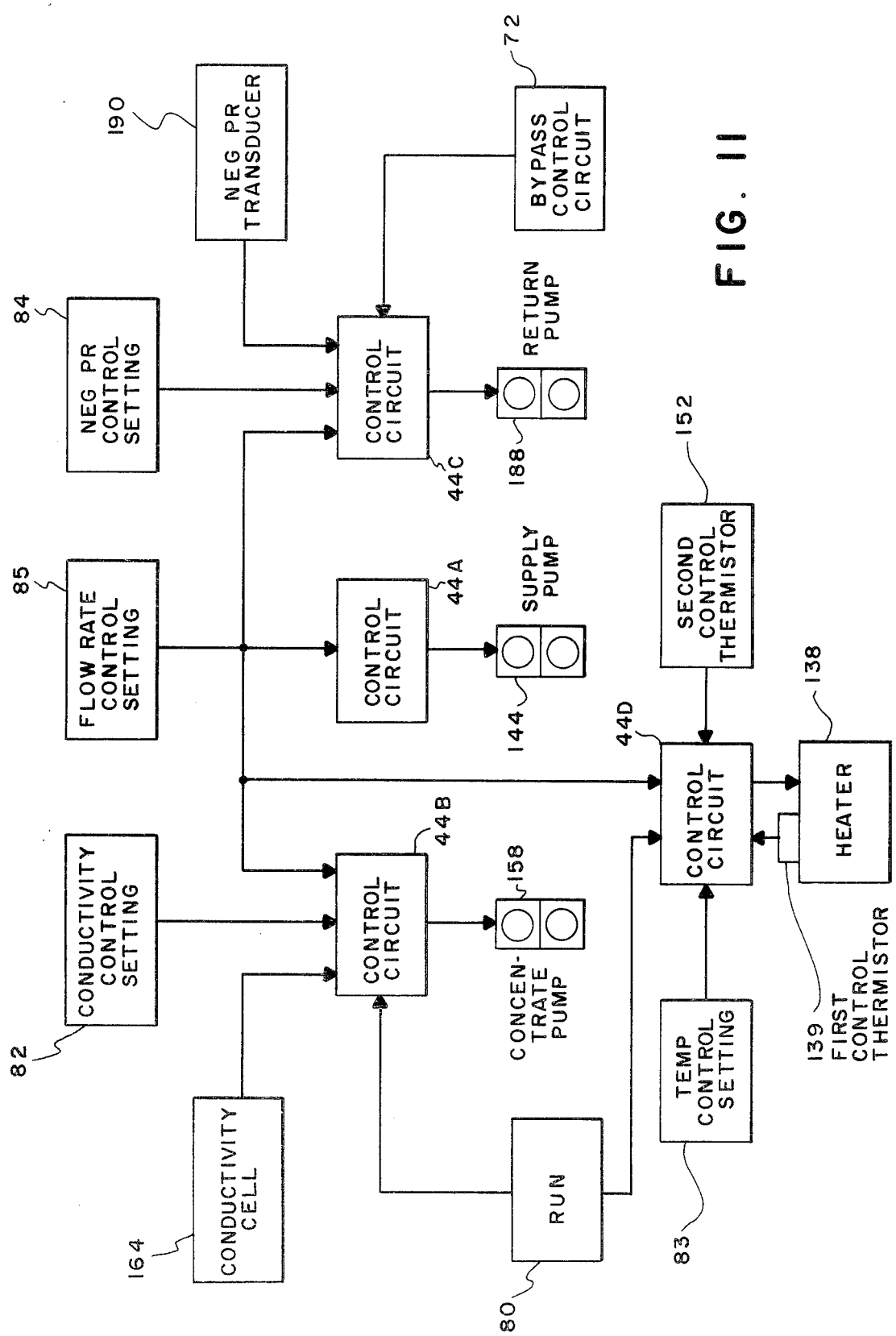
FIG. 11 is a block diagram illustrating various control functions of the present invention.

Now referring to FIG. 11, further details of the control circuit 44 will be discussed. The speed of the supply pump 144 is fixed by the dialysate flow rate setting 85, which is adjustable on the front panel 74, and which is communicated to control circuit portion 44A for driving the supply pump 144.

The speed of the concentrate pump 158 is also controlled by the dialysate flow rate setting 85. Additionally, when the RUN switch 80 is engaged, the speed of the concentrate pump 158 is controlled by the conductivity setting 82 and the feedback from the control conductivity cell 164, by means of control circuit portion 44B.

The speed of the return pump 188 is also controlled by the flow rate setting 85. Additionally, the bypass control circuit 72 sends a signal to control circuit portion 44C which controls pump 188, so that whenever the system is operating in either the supply or dialyze modes, the speed of the return pump 188 is adjusted in accordance with the negative pressure setting 84 and feedback from the negative pressure transducer 190. As an alternative to using the negative pressure value from transducer 190 as feedback for adjusting the speed of the return pump 188, it is possible to use an internally calculated value of TMP.

If the machine 10 enters the alarm mode causing the 3-way valve 184 to switch to the bypass position as discussed above, the bypass control circuit 72 causes the control circuit 44C to reference the return pump 188 to the supply pump voltage so that pumps 144 and 188 will run at essentially the same speed. Only when the system is in the supply or dialyze modes is it necessary for the return pump 188 to pull a negative pressure by outplacing the supply pump 144, thereby developing a transmembrane pressure in the artificial kidney sufficient for proper dialysis. When the machine 10 enters the supply mode, dialysate starts flowing through the artificial kidney. Typically, the pressure limit settings are initially spread wide and only narrowed when the system has stabilized in the dialyze mode.

Power to the heater 138 is supplied whenever the RUN switch 80 is engaged. The heater 138 is pulsed on and off repetitively in fixed-time intervals. The on-time pulse duration is regulated by the temperature setting 83 with an adjustment for flow rate 85, and by feedback to circuit portion 44D from thermistors 139 and 152.

Figure 12:
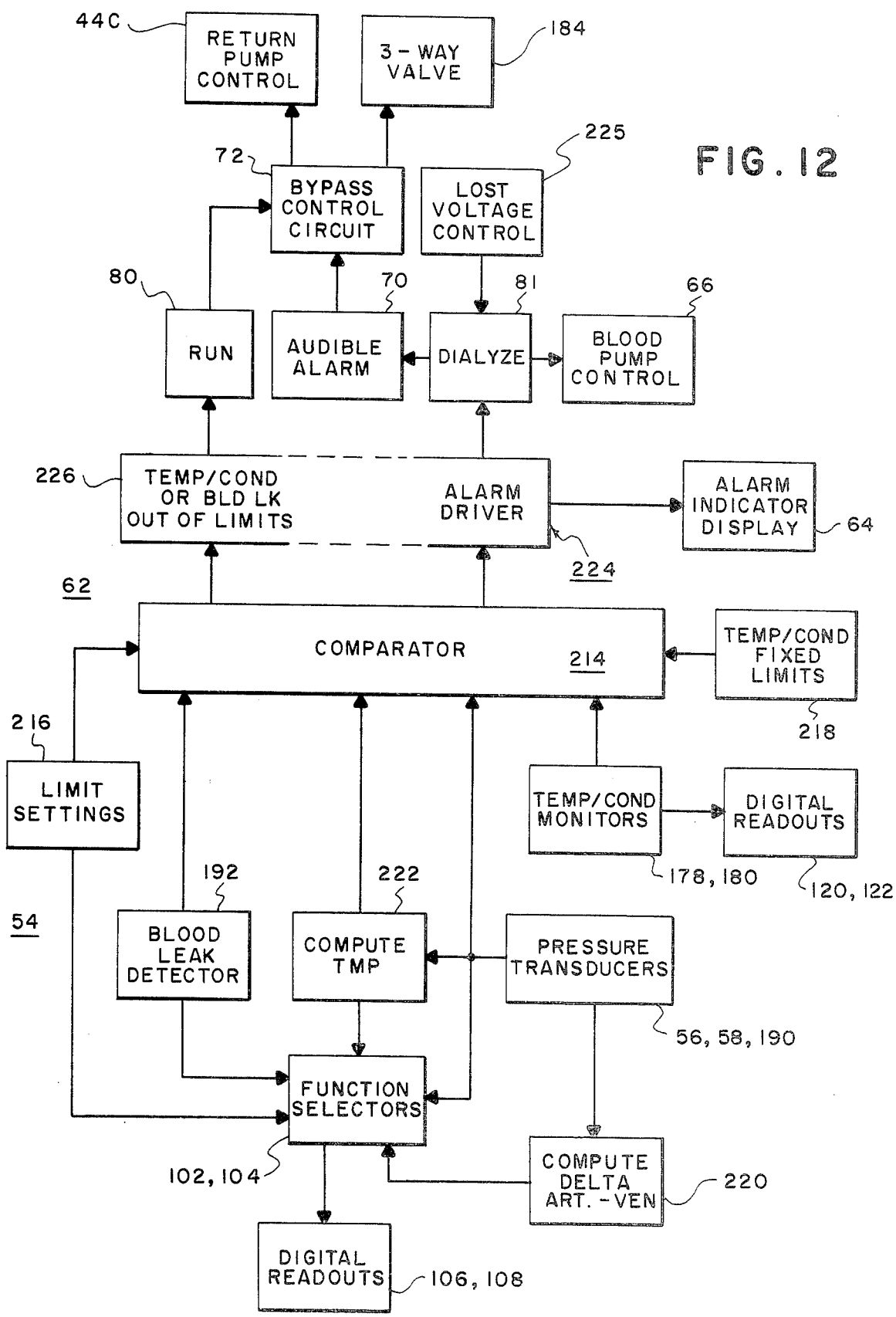
FIG. 12 is a block diagram illustrating various monitor and alarm functions of the present invention.

Now referring to FIG. 12, additional details of the monitor and alarm circuits are shown in block diagram form. A comparator circuit 214 provides a means for detection of out-of-limits conditions. The comparator circuit 214 receives limits data from the limit settings 216 from the monitor portion 100 of the front panel 74. The comparator 214 also receives internally fixed limits data 218 providing maximum and minimum limits for both dialysate temperature and conductivity.

Figure 4:
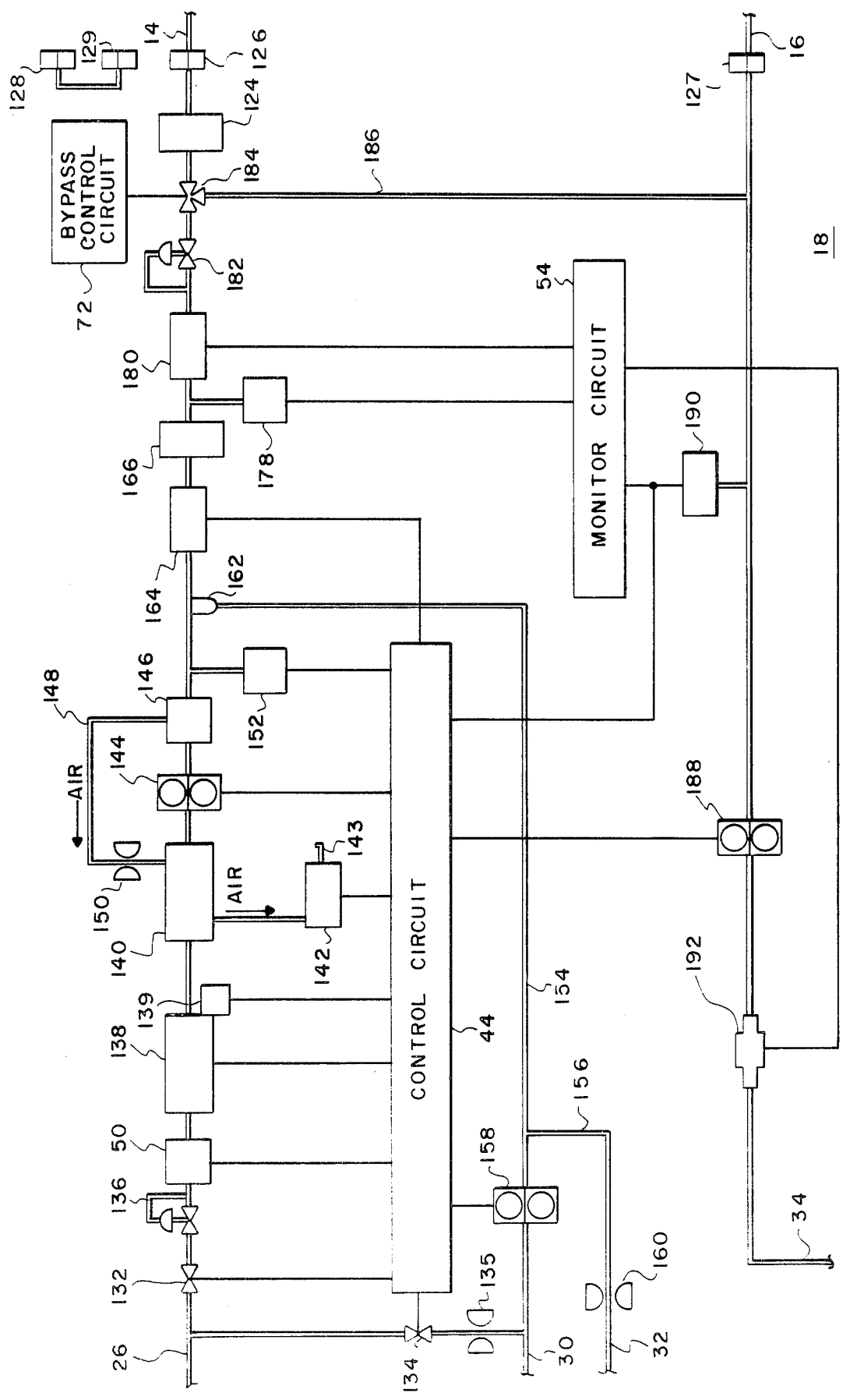
FIG. 4 is a flow diagram schematically illustrating components of a hydraulics circuit in a machine of the present invention.

The monitor circuit 54 provides the comparator 214 with real-time readings from a number of monitor transducers including the temperature and conductivity monitors 178 and 180 (see FIG. 4), the pressure tranducers 56, 58 and 190 (see FIGS. 1 and 4), and the blood leak detector 192 (see FIG. 4). Temperature and conductivity data are continuously displayed on digital readouts 120 and 122 (see FIG. 2). Pressure and blood leak data are selectively displayed on digital readouts 105 and 106 depending on the position of multi-function selector switches 102 and 104 (see FIG. 2). In addition, the monitor circuit 54 computes a value 220 of blood pressure "delta" for display purposes, which equals the difference between the readings of the arterial and venous pressure transducers 56 and 58. Lastly, the monitor circuit 54 computes a value 222 for transmembrane pressure (TMP) for both display and comparison purposes.

When the comparator 214 detects any out-of-limits condition by referencing monitor readings to either internally fixed or externally selected limits, a signal is sent to an alarm driver circuit 224, which turns on an appropriate light in the alarm indicator display 64 on the front panel 74. If any out-of-limits condition is detected when the DIALYZE switch 81 is engaged, the alarm driver 224 turns off the blood pump by means of control circuit 66 as described in FIG. 3. Also, if the DIALYZE switch 81 is engaged coincident with detection of an out-of-limits condition, the alarm driver 224 sounds the audible alarm 70 and triggers the bypass control circuit 72, which in turn puts the 3-way valve 184 into the bypass position in accordance with the alarm mode of operation described above in FIG. 10.

A lost voltage control circuit 225 is activated by engaging the DIALYZE switch 81, which causes the audible alarm 70 to sound whenever there is a loss of power either by virtue of an external power failure or by inadvertently pushing the OFF switch 79. Additional details of the lost voltage control circuit 225 will be discussed below with reference to FIG. 14.

The supply and set-up modes of operation described above in FIGS. 8 and 10 occur when the RUN switch 80 is engaged and the DIALYZE switch 81 is disengaged. The machine 10 passes from the set-up mode to the supply mode automatically when a signal is sent to the bypass control circuit 72 from a portion 226 of the alarm driver circuit 224 indicating that all three parameters of temperature, conductivity and blood leak have come within limits. The bypass control circuit 72 not only controls the position of the 3-way valve 184, but also enables feedback control of the return pump 188 by means of the control circuit portion 44C.

It will be appreciated by those skilled in the art that the sterilize and purge modes depend only on the positions of the command switches 75, while the remaining four modes of operation depend both on command switch positions and the state of the various monitored dialysate parameters with respect to their limits. Furthermore, since all limits are either internally fixed (i.e., conductivity and temperature) or held within calibrated limits (e.g., blood leak sensitivity may be set no higher than 700 ppm), the modes of set-up, supply, dialyze, and alarm are semi-automatic. In other words, the degree of control available to the operator is limited to the adjustment of the blood leak sensitivity and the various pressure parameter limits by means of the limit settings in the monitor portion 100 of the panel 74. Accordingly, it will be seen that there are no provisions for manually overriding an out-of-limits condition for temperature or conductivity to improperly initiate dialysis (i.e., improperly enter the dialyze mode). Nor can dialysis be performed with a blood leak reading in excess of 700 ppm. Nor can dialysis be performed with any pressure parameter reading outside the limits set within portion 100 of the panel 74.

The dialysate delivery machine 10 described above may be used with a wide variety of commercially available artificial kidneys. There are two principal types of artificial kidney: single pass and recirculating.

The single pass type artificial kidney, which is the type depicted in FIG. 1, is a closed system which operates by developing a negative pressure on the dialysate side of the semipermeable membrane 13. Such negative pressure is effective to develop the necessary pressure differential across the semipermeable membrane 13 for removing excess body fluids from the patient's blood.

The recirculating type artificial kidney, which is typically a coil arrangement, is open to the atmosphere on the dialysate side of its semipermeable membrane. Ordinarily it is the practice to increase the pressure of the blood entering such a recirculating type artificial kidney in order to develop the necessary transmembrane pressure. However, such recirculating type artificial kidneys may be adapted for use with the machine 10 of the present invention in an entirely satisfactory manner by means of a device which will now be discussed in conjunction with FIG. 13.

Illustrated in FIG. 13 is device 230 for adapting a recirculating type artificial kidney 232 for use with the machine 10 previously described. The device 230 comprises a canister or tank 234 for developing a negative pressure therein, and a pump 236 for recirculating dialysate contained within the tank 234. The artificial kidney 232 is mounted in the tank 234 standing on end with an inlet means 238 for receiving a dialysate input line 240 at the bottom thereof, and tubes 242 and 244 for receiving and returning the patient's blood.

The artificial kidney 232 has a semipermeable membrane (not shown) which permits removal of toxins and water from the blood in a known manner when dialysate is pumped into line 240 so that it flows out the top of the kidney 232 in a fountain-like manner as indicated by the arrows 246, while blood enters and returns through lines 242 and 244. A standpipe 248 is provided so that dialysate is allowed to form a reservoir 250 of a predetermined height in the tank 234.

Fresh dialysate is supplied to the kidney 232 by dialysate supply line 14 which is connected to the pump 236. Dialysate flows from the reservoir 250 into the standpipe 248 and back to the machine 10 through dialysate return line 16. A tube 252 is provided in the bottom of the tank 234 for recirculating dialysate by means of pump 236 through the artificial kidney 232. Vacuum seals 254 are provided as shown around each entry and exit to the tank 234.

The machine 10 of the present invention is capable of producing the required negative pressure in the tank 234 independent of the supply rate of dialysate to the tank 234, because the machine 10 has separately controllable supply and return pumps. (See pumps 144 and 188 in FIG. 4). Since the return pump 188 is self-priming, it rapidly develops the desired negative pressure by drawing air from the tank 234 prior to the reservoir 250 reaching its maximum height.

Thus it is seen that the device 230 of FIG. 13 permits development of a negative pressure on the dialysate side of the semipermeable membrane of the recirculating type artificial kidney 232, thereby eliminating the necessity of raising the pressure on the blood side of the membrane with attendant safety advantages for the patient.

FIG. 14 illustrates one possible arrangement for triggering the audible alarm 70. A rechargeable battery 260 is connected in parallel with a battery charger 262, which recharges the battery 260 when AC power is supplied to the machine 10. The battery 260 is capable of sounding the audible alarm 70 by connection through either of two possible switch paths.

A normally closed switch contact 225 is opened whenever power is on. A normally open switch contact 264 is closed whenever the DIALYZE switch 81 is engaged. Thus, the series combination of the switches 225 and 264 provides means for sounding the alarm 70 whenever there is a loss of system power coincident with a DIALYZE command.

A normally open switch contact 266 is caused to close by the alarm driver circuit 224 (see FIG. 12) whenever any out-of-limits condition is detected, which causes the alarm 70 to sound coincident with a DIALYZE command.

Although a preferred embodiment of the invention has been described in detail, it is to be understood that various changes, substitutions and alterations can be made therein without departing from the spirit and scope of the invention as defined by the appended claims.

What is claimed is:

1. An apparatus for delivering a dialysate solution to an artifical kidney device comprising:
   a hydraulics circuit, the hydraulics circuit having a water supply branch, a dialysate solution supply branch extending from the junction of the water supply branch and the dialysate concentrate supply branch to a port for supplying dialysate solution to an artifical kidney, and a return branch extending from a port through which dialysate solution returns from the artifical kidney to a drain line for passing used dialysate solution out of the hydraulics circuit;
   a supply pump disposed in the water supply branch for pumping water into the dialysate solution supply branch at a controlled rate;
   means for controllably heating water flowing in the water supply branch;
   means downstream from the heating means for deaerating water flowing in the water supply branch;
   a concentrate pump disposed in the dialysate concentrate supply branch for pumping dialysate concentrate into the dialysate solution supply branch at a controlled rate;
   a return pump disposed in the return branch for drawing effluent dialysate solution from the artifical kidney and pumping the solution out through the drain line;
   a first transducer for generating an electrical signal representative of the negative pressure in the return branch upstream from the return pump;
   a second transducer for generating an electrical signal representative of arterial pressure in the artificial kidney;
   a third transducer for generating an electrical signal representative of venous pressure in the artificial kidney; and
   first electrical circuit means for controlling the speed of the return pump in response to the electrical signals from the first, second and third transducers in a combination representative of transmembrane pressure such that the speed of the return pump maintains a predetermined transmembrane pressure in the artifical kidney.

2. The apparatus of claim 1 further comprising:
a concentrate inlet line joining the dialysate concentrate supply branch upstream from the concentrate pump for drawing dialysate concentrate from a container;
a concentrate outlet line for returning unused dialysate concentrate to the container;
an interconnecting branch joining the concentrate outlet line to the dialysate concentrate supply line at a point in the dialysate concentrate supply line downstream from the concentrate pump; and
means for restricting the flow of dialysate concentrate through the interconnecting branch such that a predetermined fraction of the dialysate concentrate passing through the concentrate pump is injected into the water flowing from the water supply branch into the dialysate solution supply branch while the remaining dialysate concentrate passing through the concentrate pump is returned to the container through the concentrate outlet line.

3. The apparatus of claim 1 further comprising:
means for generating an electrical signal representative of the conductivity of the dialysate solution flowing in the dialysate solution supply branch;
electrical circuit means for controlling the speed of the concentrate pump in response to the electrical signal from the generating means to provide a flow of dialysate solution of a predetermined conductivity; and
means for manually adjusting the predetermined conductivity value within a defined range of compensate for ions in the water supply.

4. The apparatus of claim 1 further comprising:
a mixing chamber disposed in the dialysate solution supply branch for damping conductivity variations in the flowing dialysate solution;
a first conductivity cell disposed in the dialysate solution supply branch upstream from the mixing chamber;
second electrical circuit means for controlling the speed of the concentrate pump in response to a signal from the first conductivity cell to regulate the conductivity of the dialysate solution;
a second conductivity cell disposed in the dialysate solution supply branch downstream from the mixing chamber; and
third electrical circuit means for comparing a signal from the second conductivity cell to predetermined limits and initiating commands for selectively controlling the delivery or nondelivery of dialysate solution from the apparatus to the artifical kidney device in response to the comparisons made.

5. The apparatus of claim 4 wherein the mixing chamber includes an inlet at an upstream end of the chamber, an outlet at a downstream end of the chamber, a tubular member disposed within the chamber and having a plurality of orifices disposed along its length, an open end of the tubular member being in fluid communication with the inlet, whereby dialysate solution flows through the inlet into the tubular member and then through the orifices into the chamber and then out through the outlet.

6. The apparatus of claim 4 further comprising:
a bypass line extending from a connection point on the dialysate solution supply branch to a connection point on the return branch; and
electrically actuable valve means at the connection of the dialysate solution supply branch and the bypass line for automatically diverting the flow of dialysate solution from the dialysate solution supply branch to the return branch in order to bypass the artificail kidney, the valve means being responsive to a command from the third electrical circuit means indicating that the conductivity of the dialysate solution is out of limits;
wherein the return pump is controlled such that it runs in synchronization with the supply pump when dialysate solution is flowing through the bypass line or when dialysate solution is flowing out to an artificial kidney coincident with a STERILIZE or PURGE command, but is servo-controlled by the first electrical circuit mmeans when dialysate solution is flowing out to an artificial kidney coincident with a RUN command.

7. The apparatus of claim 6 further comprising means for manually controlling the speed of the supply pump to achieve a desired flow rate.

8. The apparatus of claim 1 further comprising means for selectively controlling a blood pump to start blood flowing into the artificial kidney in response to an enabling signal from an alarm circuit coincident with RUN and DIALYZE commands from a control panel.

9. The apparatus of claim 1 further comprising a control panel, the panel including at least one electronic readout device, means for setting various parameter limits, and a switch for selectively displaying any one of several parameter readings or parameter limit settings on the readout device.

10. The apparatus of claim 1, wherein the deaerating means comprises:
a float tank upstream from the supply pump for containing controlled volume of water;
means for pulling a partial vacuum on the float tank to remove air bubbles from the water;
a deaerator downstream from the supply pump for removing additional air bubbles from the water;
a line interconnecting the top of the deaerator to the top of the float tank to permit air flow from the deaerator to the float tank; and
a restriction disposed in the interconnecting line for maintaining a positive pressure in the deaerator.

11. The apparatus of claim 10 further comprising:
means disposed in the water supply branch upstream from the heating means for sensing water pressure;
a manually engageable STERILIZE command switch on a panel of the apparatus;
electrical circuit means operable when power is supplied to the apparatus for selectively permitting operation of the heating means and the pumps in response to the sensing means and STERILIZE command switch, such that the heating means and pumps are operable whenever the STERILIZE command switch is disengaged coincident with the sensing means detecting a water pressure above a predetermined minimum level, and such that the heating means is inoperable and the pumps are operable whenever the STERILIZE command switch is engaged regardless of the water pressure detected by the sensing means;
whereby, when the STERILIZE command switch is engaged, the combined suction of the supply pump and the means for pulling partial vacuum on the float tank enable cleansing fluid to be rapidly drawn into the water supply branch through an inlet line interconnecting the upstream end of the water supply branch and an unpressurized container of cleansing fluid.

12. A system for dialyzing the blood of a kidney-failure patient, comprising:

an artificial kidney including entry and return lines for the patient's blood, a bottom portion including inlet means for receiving dialysate solution and a top portion for permitting dialysate solution to flow out in a fountain-like manner;

a device for developing a negative pressure on the dialysate solution flowing through the artificial kidney, the device including a tank for isolating the artificial kidney from the atmosphere, means for holding the artificial kidney in an upright position in the tank, a dialysate input line for supplying dialysate solution to the bottom of the artificial kidney, a standpipe in the tank having an open top for draining the dialysate solution thereby permitting the dialysate solution to form and maintain a reservoir of a predetermined height below the top of the artificial kidney in the tank, means for recirculating dialysate solution from the reservoir back through the artifical kidney, and vacuum seal means for permitting ingress and egress of the various fluid carrying lines through the walls of the tank; and a dialysate delivery machine including means for controllably proportioning water and dialysate concentrate to provide dialysate solution, means in fluid communication with the recirculating means for delivering dialysate solution from the machine to the artificial kidney, means in fluid communication with the bottom of the standpipe for returning the overflow of dialysate solution from the standpipe to the machine, a return pump for drawing air and dialysate solution from the tank through the standpipe, the return pump being capable of developing a negative pressure in the tank, and means for regulating the negative pressure in the return line within defined limits thereby maintaining a desired value of negative pressure in the tank.

13. An apparatus for delivering a dialysate solution to an artificial kidney device comprising:

a hydraulics circuit, the hydraulics circuit having a water supply branch, a dialysate concentrate supply branch joined at one end to the water supply branch, a dialysate solution supply branch extending from the junction of the water supply branch and the dialysate concentrate supply branch to a port for supplying dialysate solution to an artificial kidney, and a return branch extending from a port through which dialysate solution returns from the artificial kidney to a drain line for passing used dialysate solution out of the hydraulics circuit;

a supply pump disposed in the water supply branch for pumping water into the dialysate solution supply branch at a controlled rate;

a concnetrate pump disposed in the dialysate concentrate supply branch for pumping dialysate concentrate into the dialysate solution supply branch at a controlled rate;

a return pump disposed in the return branch for drawing effluent dialysate from the artificial kidney and pumping the solution out through the drain line;

a mixing chamber disposed in the dialysate solution supply branch for damping conductivity variations in the flowing dialysate solution;

a first conductivity cell disposed in the dialysate solution supply branch upstream from the mixing chamber;

electrical circuit means for controlling the speed of the concentrate pump in response to a signal from the first conductivity cell to regulate the conductivity of the dialysate solution;

a second conductivity cell disposed in the dialysate solution supply branch downstream from the mixing chamber; and electrical circuit means for comparing a signal from the second conductivity cell to predetermined limits and initiating commands for selectively controlling the delivery or nondelivery of dialysate solution from the apparatus to the artifical kidney device in response to the comparisons made.

14. The apparatus of claim 13 wherein the mixing chamber includes an inlet at an upstream end of the chamber, an outlet at a downstream end of the chamber, a tubular member disposed within the chamber and having a plurality of orifices disposed along its length, an open end of the tubular member being in fluid communication with the inlet, whereby dialysate solution flows through the inlet into the tubular member and then through the orifices into the chamber and then out through the outlet.

* * * * *